United States Patent
Cheney et al.

(10) Patent No.: US 9,821,378 B2
(45) Date of Patent: Nov. 21, 2017

(54) DRILL GUIDE AND METHOD OF MANUFACTURE THEREOF

(71) Applicant: BioMedical Enterprises, Inc., San Antonio, TX (US)

(72) Inventors: Daniel F. Cheney, San Antonio, TX (US); Adam T. Knight, San Antonio, TX (US); Joseph P. Ritz, San Antonio, TX (US)

(73) Assignee: BioMedical Enterprises, Inc., San Antonio, TX (US)

( * ) Notice: Subject to any disclaimer, the term of this patent is extended or adjusted under 35 U.S.C. 154(b) by 359 days.

(21) Appl. No.: 14/823,726

(22) Filed: Aug. 11, 2015

(65) Prior Publication Data
US 2017/0043415 A1    Feb. 16, 2017

(51) Int. Cl.
| A61B 17/58 | (2006.01) |
| A61B 17/60 | (2006.01) |
| A61F 2/00 | (2006.01) |
| B23B 49/02 | (2006.01) |
| A61B 17/064 | (2006.01) |
| A61B 17/17 | (2006.01) |

(52) U.S. Cl.
CPC ........ *B23B 49/023* (2013.01); *A61B 17/0642* (2013.01); *A61B 17/17* (2013.01); *B23B 2260/026* (2013.01)

(58) Field of Classification Search
None
See application file for complete search history.

(56) References Cited

U.S. PATENT DOCUMENTS

| 5,743,916 | A | 4/1998 | Greenberg |
| 7,625,378 | B2 | 12/2009 | Foley |

(Continued)

FOREIGN PATENT DOCUMENTS

| EP | 0358372 A1 | 3/1990 |
| EP | 1967143 B1 | 9/2008 |
| EP | 2702956 A1 | 3/2014 |

OTHER PUBLICATIONS

SPEED™ Continuous Compression Fixation System Brochure, © 2011, BioMedical Enterprises, Inc., 14875 Omicron Drive, Suite 205, San Antonio, TX 78245.

(Continued)

*Primary Examiner* — Sameh Boles
(74) *Attorney, Agent, or Firm* — Christopher L. Makay

(57) ABSTRACT

A drill guide includes a shaft, a drill guide assembly securable to the shaft, and a first drill guide insert. The drill guide assembly includes a first drill guide body defining a receiving passage, a locking member, and terminating in a first grasping projection that flexes between open and closed positions. The first drill guide insert installs in the receiving passage and includes a bore, a grasping projection displacement surface, a locking groove, and a key member. The grasping projection displacement surface moves the first grasping projection from its closed position to its open position during installation of the first drill guide insert. Upon installation, the locking groove receives the first grasping projection to lock the first drill guide insert in the first drill guide body, and the key member engages the locking member to prevent rotation of the first drill guide insert within the first drill guide body.

14 Claims, 10 Drawing Sheets

(56) References Cited

U.S. PATENT DOCUMENTS

| | | |
|---|---|---|
| D630,746 S | 1/2011 | Richter et al. |
| D669,984 S | 10/2012 | Cheney et al. |
| 8,584,853 B2 | 11/2013 | Knight et al. |
| 2003/0083667 A1 | 5/2003 | Ralph et al. |
| 2004/0102788 A1 | 5/2004 | Huebner |
| 2004/0193173 A1* | 9/2004 | Knopfle ............. A61B 17/1728 606/96 |
| 2011/0152870 A1 | 6/2011 | Miniaci et al. |
| 2012/0253353 A1 | 10/2012 | McBride |
| 2013/0213843 A1 | 8/2013 | Knight et al. |
| 2013/0289447 A1 | 10/2013 | Cavallazzi et al. |
| 2014/0316418 A1 | 10/2014 | Blain et al. |

OTHER PUBLICATIONS

SPEED™ Continuous Compression Fixation System Brochure, © 2012, BioMedical Enterprises, Inc., 14875 Omicron Drive, Suite 205, San Antonio, TX 78245.

REVERTO™ Shape Memory Stapel System for Arthrodesis and Skeletal Fixation of the Hand Brochure, © 2009, Core Essence Orthopedics, Inc., 301 Oxford Valley Road, Suite 905B, Yardley, PA 19067.

METRIC™ Super Staple Brochure, © 2013, Metric Medical Devices, Inc., 846 Silver Springs, Helotes, TX 78023.

EASY CLIP™ SI Superelastic Fixation System Brochure, © 2009, MMI-USA, 6060 Poplar Ave., Suite 254, Memphis, TN 38119.

FUSEFORCE™ SuperElastic, Shape Memory Nitinol Brochure, © 2013, Solana Surgical, LLC, 6363 Poplar Ave. Memphis, TN 38119.

TRIMED™ Highly Elastic Staples Surgical Technique Brochure, © 2013, TriMed, Inc.. 27533 Avenue Hopkins, Valencia, CA 91355.

SPEED™ Continuous Compression Fixation System Brochure with Overmolded Drill Guide, © 2015, BioMedical Enterprises, Inc., 14875 Omicron Drive, Suite 205, San Antonio, TX 78245.

SPEED™ Continuous Compression Fixation System Brochure with Overmolded Drill Guide, © 2014, BioMedical Enterprises, Inc., 14875 Omicron Drive, Suite 205, San Antonio, TX 78245.

\* cited by examiner

DRILL GUIDE AND METHOD OF MANUFACTURE THEREOF

BACKGROUND OF THE INVENTION

1. Field of the Invention

The present invention relates generally to a drill guide assembly and, more particularly, but not by way of limitation, to a drill guide assembly for use with medical devices and a method of manufacture thereof.

2. Description of the Related Art

Medical implants designed for use in orthopedics typically require a surgeon to drill holes into the bone in order to install the implant. Holes drilled into the bone freehand leave the potential for misalignment of the implant once installed into the bone. To prevent misalignment of the implant, a drill guide is frequently used to help guide the drill bit and ensure proper angulation and separation distance for each drill hole.

To reduce costs and simplify logistics in the operating room, medical device manufacturers prefer to use pre-sterilized and disposable drill guides. In making drill guides, materials such as plastic are preferred. Plastic drill guides can be injection molded in large quantities thereby reducing costs. However, drill guides made solely of plastic typically are not suitable for orthopedic surgery on the basis drill bits used in orthopedic surgery are normally made of metal. Metal drill bits spinning at high speed within a drill guide may create plastic shavings, which would drop into the patient during surgery. Making the drill guide solely from a material such as metal to prevent the creation of plastic shavings would be cost prohibitive. Therefore, medical device manufacturers frequently use metal guides inserted within a plastic body.

A metal guide inserted within a plastic body has several benefits. The metal guide prevents the drill bit from creating plastic shavings that drop into a patient during surgery while the plastic body allows for inexpensive mass production. The plastic body is typically manufactured using injection molding and the metal guides are then machined and attached to the plastic body by overmolding or press fit. In overmolding, molten plastic is poured around a metal guide during the injection molding process. An example of over-molded plastic drill guides with metal tubes is the BME Speed™ fixation system (BioMedical Enterprises, Inc, San Antonio, Tex.). The BME Speed™ fixation system has been on sale in the United States since 2011. In press fitting, the metal guides are inserted into the plastic body after the injection molding process. Both over molding and press fitting have disadvantages. In the overmolding process, it is more difficult to automate the injection molding process when a metal guide has to be positioned in the mold for each part. In press fitting, the tube receiving the metal guide must be a precise diameter. Creating a precise diameter of the tube ensures the metal guide remains firmly attached to plastic body while simultaneously preventing cracking of the plastic body. This however increases the manufacturing costs of the drill guide. Furthermore, drill guides that use press fits are also susceptible to rotation if the drill bit grasps the metal guide while spinning at high speeds.

Accordingly, a drill guide incorporating a metal guide or guides mated with a plastic body that is manufactured in such a way that overcomes the disadvantages of press fitting and overmolding would be beneficial.

SUMMARY OF THE INVENTION

In accordance with the present invention, a drill guide includes a shaft, a drill guide assembly securable to the shaft, and a first drill guide insert. The drill guide assembly includes a first drill guide body defining a receiving passage. The first drill guide body includes a locking member and terminates in a first grasping projection adapted for flexing between an open position and a closed position. To allow the first grasping projection of the first drill guide body to flex between the open and the closed position, the first drill guide body includes a first slot and a second slot with the first grasping projection therebetween.

The first drill guide insert defines a bore and inserts into the receiving passage of the first drill guide body. The first drill guide insert includes a grasping projection displacement surface, a locking groove, and a key member. The grasping projection displacement surface engages and moves the first grasping projection from its closed position to its open position during initial insertion of the first drill guide insert into the receiving passage of the first drill guide body. During continued insertion of the first drill guide insert into the receiving passage, the grasping projection displacement surface disengages from the first grasping projection such that the first grasping projection moves from its open position to its closed position and engages the locking groove of the first drill guide insert. Upon the first grasping projection engaging the locking groove, the first drill guide insert is prevented from being pushed through or pulled out of the receiving passage of the first drill guide body. Furthermore, during the continued insertion of the first drill guide insert into the receiving passage of the first drill guide body, the key member engages the locking member of the first drill guide body thereby preventing rotation of the first drill guide insert within the receiving passage of the first drill guide body.

The drill guide assembly of the drill guide may include a second drill guide body and a platform connecting the first and second drill guide bodies. The platform spaces the first and second drill guide bodies apart from each other a distance substantially equal to a distance between first and second legs of an implant residing in an open insertion position. In the preferred embodiment, the second drill guide body is substantially similar to the first drill guide body. Likewise, a second drill guide insert, which is substantially similar to the first drill guide insert, installs within the second drill guide body.

The drill guide assembly of the drill guide may further include a third drill guide body. The platform connects the first, second, and third drill guide bodies and further spaces the first, second, and third drill guide bodies apart from each other distances substantially equal to distance among first, second, and third legs of an implant residing in an open insertion position. In the preferred embodiment, the third drill guide body is substantially similar to the first and second drill guide bodies. Likewise, a third drill guide insert, which is substantially similar to the first and second drill guide inserts, installs within the third drill guide body.

The drill guide may be manufactured using the following method. A drill guide body assembly and a shaft are formed integrally from a plastic material using injection molding techniques. The drill guide body assembly includes a first drill guide body. The first drill guide body defines a receiving passage including a locking member. The first drill guide body terminates in a first grasping projection adapted for flexing between an open position and a closed position.

A first drill guide insert is formed from a metal material. The first drill guide insert defines a bore and is adapted for insertion into the receiving passage of the first drill guide body. The first drill guide insert includes a grasping projection displacement surface, a locking groove, and a key member.

The first drill guide insert installs within the receiving passage of the first drill guide body until the grasping projection displacement surface engages and moves the first grasping projection from its closed position to its open position. Insertion of the first drill guide insert within the receiving passage continues until the key member engages the locking member thereby preventing rotation of the first drill guide insert within the receiving passage. Furthermore, insertion of the first drill guide insert within the receiving passage continues until the grasping projection displacement surface disengages from the first grasping projection such that the first grasping projection moves from its open position to its closed position, resulting in the first grasping projection engaging the locking groove thereby preventing the first drill guide insert from being pushed through or pulled out of the receiving passage of the first drill guide body.

Manufacture of the drill guide may include forming the drill guide body assembly and the shaft integrally from a plastic material such that the drill guide body assembly includes a second drill guide body substantially similar to the first drill guide body and a platform connecting the first drill guide body with the second drill guide body. The platform spaces the first drill guide body apart from the second drill guide body a distance substantially equal to a distance between first and second legs of an implant residing in an open insertion position. Likewise, a second drill guide insert, which is substantially similar to the first drill guide insert, is formed from a metal material. The second drill guide insert installs within the second drill guide body substantially similar to the installation of the first drill guide insert within the first drill guide body.

Manufacture of the drill guide may further include forming the drill guide body assembly and the shaft integrally from a plastic material such that the drill guide body assembly includes a third drill guide body substantially similar to the first and second drill guide bodies and a platform connecting the first, second, and third drill guide bodies. The platform spaces the first, second, and third drill guide bodies distances substantially equal to distances among first, second, and third legs of an implant residing in an open insertion position. Likewise, a third drill guide insert, which is substantially similar to the first and second drill guide inserts, is formed from a metal material. The third drill guide insert installs within the third drill guide body substantially similar to the installations of the first and second drill guide inserts within the first and second drill guide bodies.

DETAILED DESCRIPTION OF THE PREFERRED EMBODIMENT

As required, a detailed embodiment of the present invention is disclosed herein; however, it is to be understood that the disclosed embodiment is merely exemplary of the invention, which may be embodied in various forms. It is further to be understood that the figures are not necessarily to scale, and some features may be exaggerated to show details of particular components or steps.

FIGS. 1-2 and 7-8 illustrate a drill guide 300. The drill guide 300 includes a drill guide body assembly 200 comprised of drill guide bodies 210-212 and a shaft 250 securable with the drill guide body assembly 200. The shaft 250 may function as a handle or may be secured with a handle using any suitable means such as a press fit to allow a surgeon to grasp and manipulate the drill guide 300. The drill guide 300 further includes a drill guide insert 100 that installs within each of the drill guide bodies 210-212 of the drill guide body assembly 200.

Figure 9:
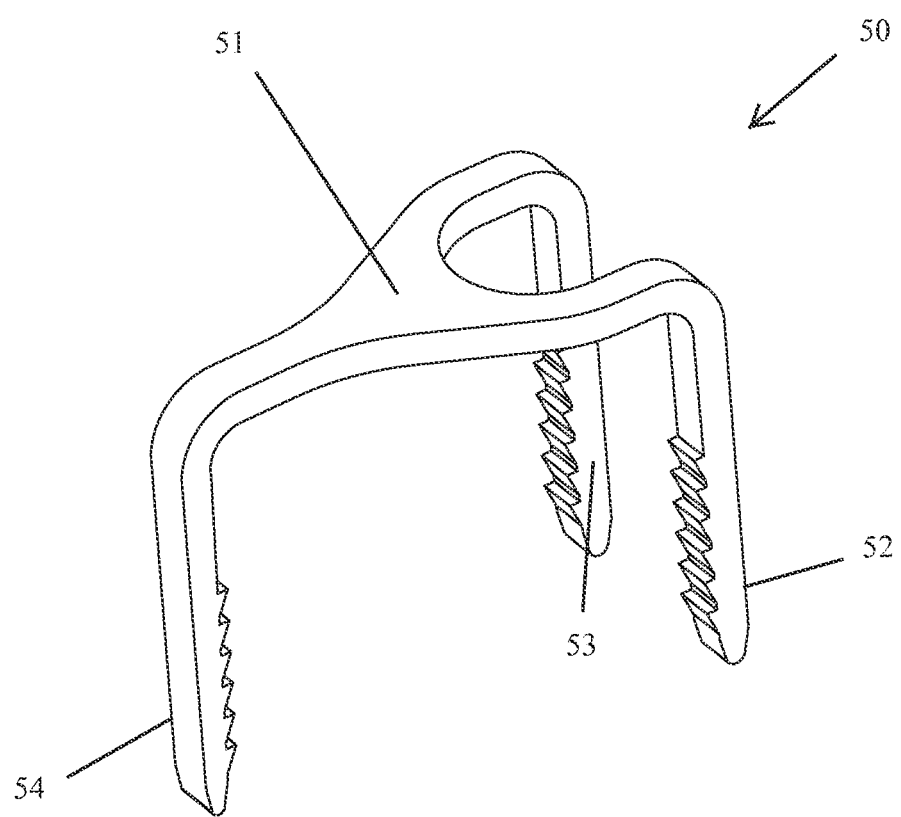
FIG. 9 is an isometric view illustrating an implant in an open insertion position.
Figure 10:
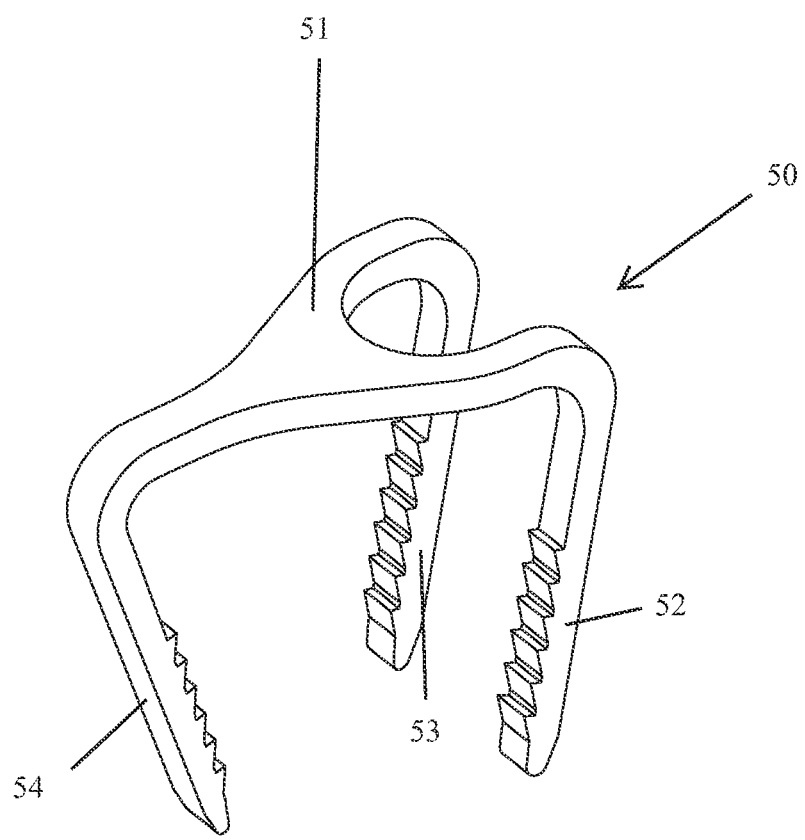
FIG. 10 is an isometric view illustrating the implant in a closed implanted position.

FIGS. 9 and 10 illustrate an example implant 50 used in conjunction with the drill guide 300. The implant 50 includes a body 51 having legs 52-54 extending therefrom. In the present invention, the implant 50 is manufactured from a shape memory material such as Nitinol to allow movement of the legs 50 between a closed implanted position shown in FIG. 10 and an open insertion position shown in FIG. 9.

The drill guide insert 100 includes a bore 102, a bone engagement surface 103, a key member 120, and a receiving cavity engagement surface 101. The bore 102 is designed to receive a drill bit such that the drill bit rotates within the bore 102 without binding inside the drill guide insert 100. The bone engagement surface 103 grips bone or tissue to maintain the drill guide 300 in place on a patient's tissue or bone. The key member 120 and the receiving cavity engagement surface 101 are designed to mate the drill guide insert 100 with one of the drill guide bodies 210-212.

The key member 120 is located at a top portion of the drill guide insert 100 and is designed to prevent rotation of the drill guide insert 100 once the drill guide insert 100 installs within one of the drill guide bodies 210-212. In the preferred embodiment, the key member 120 includes individual flat surfaces producing a hexagonal shape. It should be noted that, although the key member 120 includes individual flat surfaces, any surface or shape suitable to prevent rotation of the drill guide 100 may be used.

The receiving cavity engagement surface 101 includes a locking groove 150 that is circumferential and a grasping projection displacement surface 151. The grasping projection displacement surface 151 is beveled and contacts a portion of the drill guide bodies 210-212 such that a portion of the drill guide bodies 210-212 move to engage the locking groove 150. In particular after the drill guide bodies 210-212 move to engage the locking groove 150, the drill guide bodies 210-212 grasp and lock the drill guide 100 within the drill guide bodies 210-212. Once the drill guide insert 100 locks within one of the drill guide bodies 210-212, the drill guide 100 insert is prevented from being pushed through or pulled out of the drill guide bodies 210-212. Furthermore, although the locking groove 150 has been described as a circumferential, the locking grove 150 could also be sections of a groove that are not circumferential or other engagement features such as notches, bumps, ridges, or the like.

The drill guide body assembly 200 in the preferred embodiment includes a platform 201 connecting the drill guide bodies 210-212. The platform 201 of the drill guide body assembly 200 connects and maintains the position of the drill guide bodies 210-212 such that the distance between the drill guide bodies 210 and 212 corresponds to the distance between the legs 52 and 54 of implant 50 in their open insertion position shown in FIG. 9, the drill guide bodies 211 and 212 corresponds to the distance between the legs 53 and 54 of implant 50 in their open insertion position shown in FIG. 9, and the drill guide bodies 210 and 211 corresponds to the distance between the legs 52 and 53 of implant 50 in their open insertion position shown in FIG. 9. While the preferred embodiment discloses the shaft 250 secured with the drill guide body 212 of the drill guide body assembly 200, one of ordinary skill in the art will recognize that the shaft 250 may be secured with the platform 201 or either of the drill guide bodies 210 and 211. The drill guide body assembly 200 can be made of any material, however, in the preferred embodiment, the drill guide body assembly 200 is made of plastic that is injection molded or machined using conventional techniques.

Each of the drill guide bodies 210-212 defines a receiving passage 255 adapted to receive a drill guide insert 100. The receiving passage 255 includes a locking member 220 and grasping projections 225. The locking member 220 engages the key member 120 of the drill guide insert 100, while the grasping projections 225 engage the receiving cavity engagement surface 101 of the drill guide insert 100.

The locking member 220 includes a number of flat surfaces that correspond to the number of flat surfaces of the key member 120. Upon insertion of the drill guide insert 100 within the receiving passage 255, the flat surfaces of the key member 120 mates with the flat surfaces of the locking member 220, thereby locking the key member 120 with the locking member 220.

The grasping projections 225 move between an open position and a closed position and each include an engagement ridge 230 that grasps the locking groove 150 of the drill guide insert 100 thereby locking the drill guide insert 100 within one of the drill guide bodies 210-212. Specifically, the grasping projection displacement surface 151 of the drill guide insert 100 engages engagement ridge 230 of the grasping projecting 225 to move the grasping projection 225 from it closed position to its open position. In the preferred embodiment, each of the drill guide bodies 210-212 includes four grasping projections 225. Furthermore, each of the grasping projections 225 are separated by a slot 226 that allows the grasping projections 225 to flex and move between their closed and open positions. While the preferred embodiment discloses four grasping projections 225, one of ordinary skill in the art will recognize that only one grasping projection is necessary and that any number of grasping projections 225 may be used.

Figure 1:
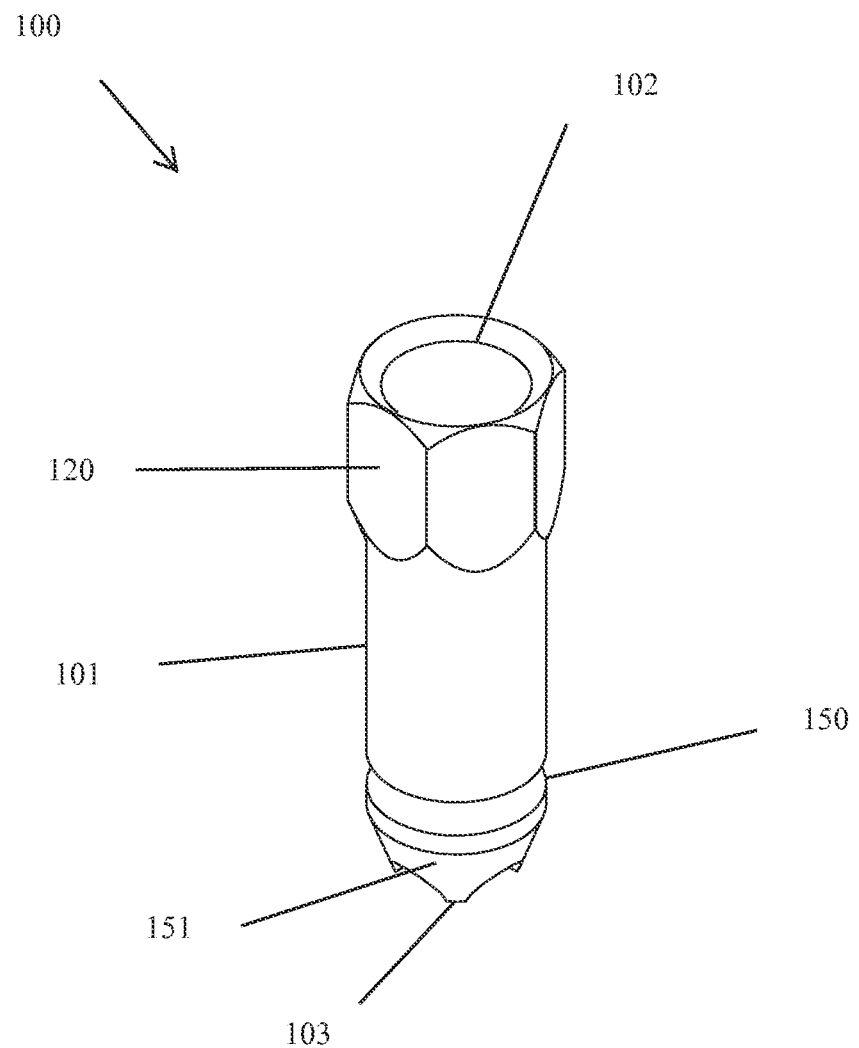
FIG. 1 is an isometric view illustrating a drill guide insert.
Figure 2:
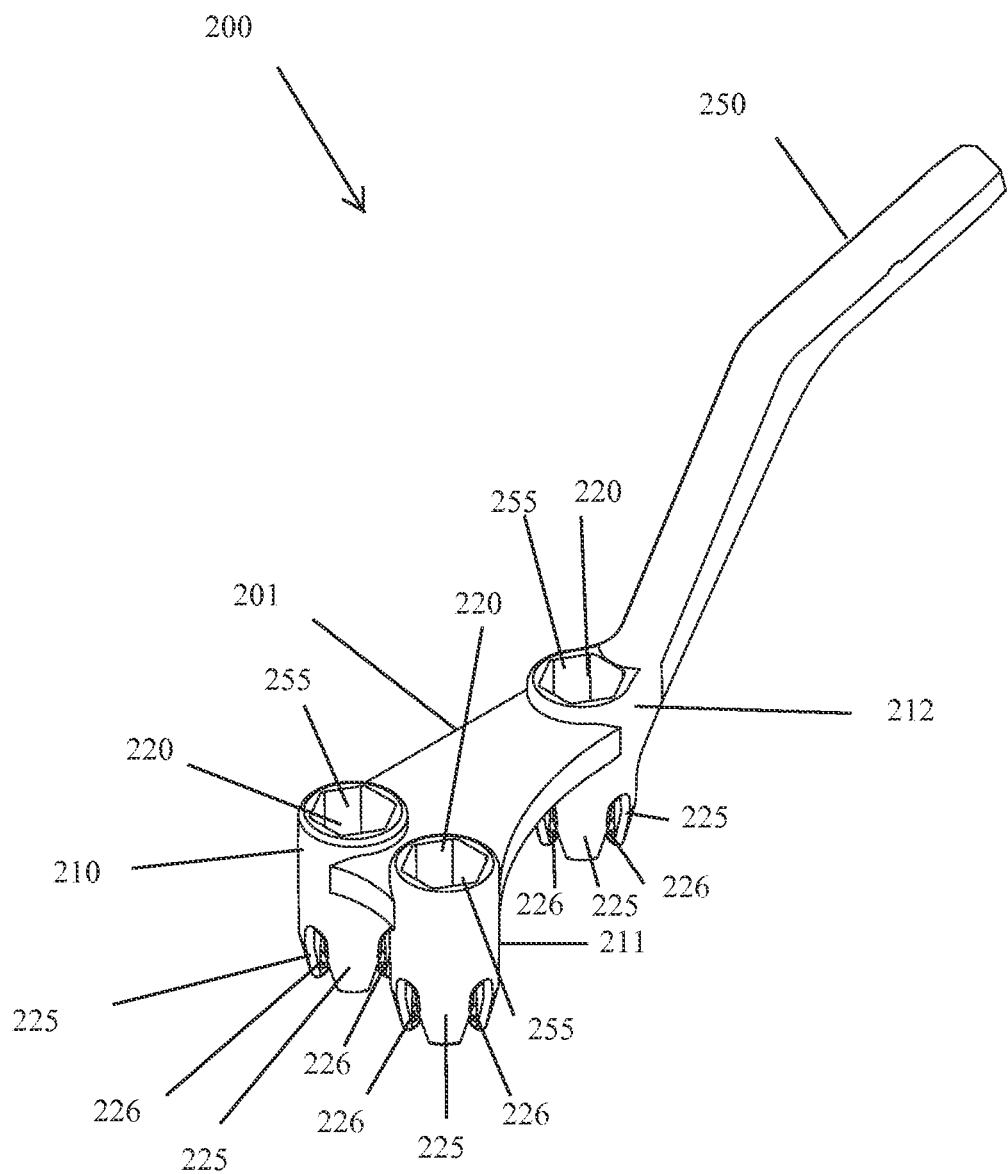
FIG. 2 is an isometric view illustrating a drill guide assembly and a handle secured to the drill guide assembly.
Figure 3:
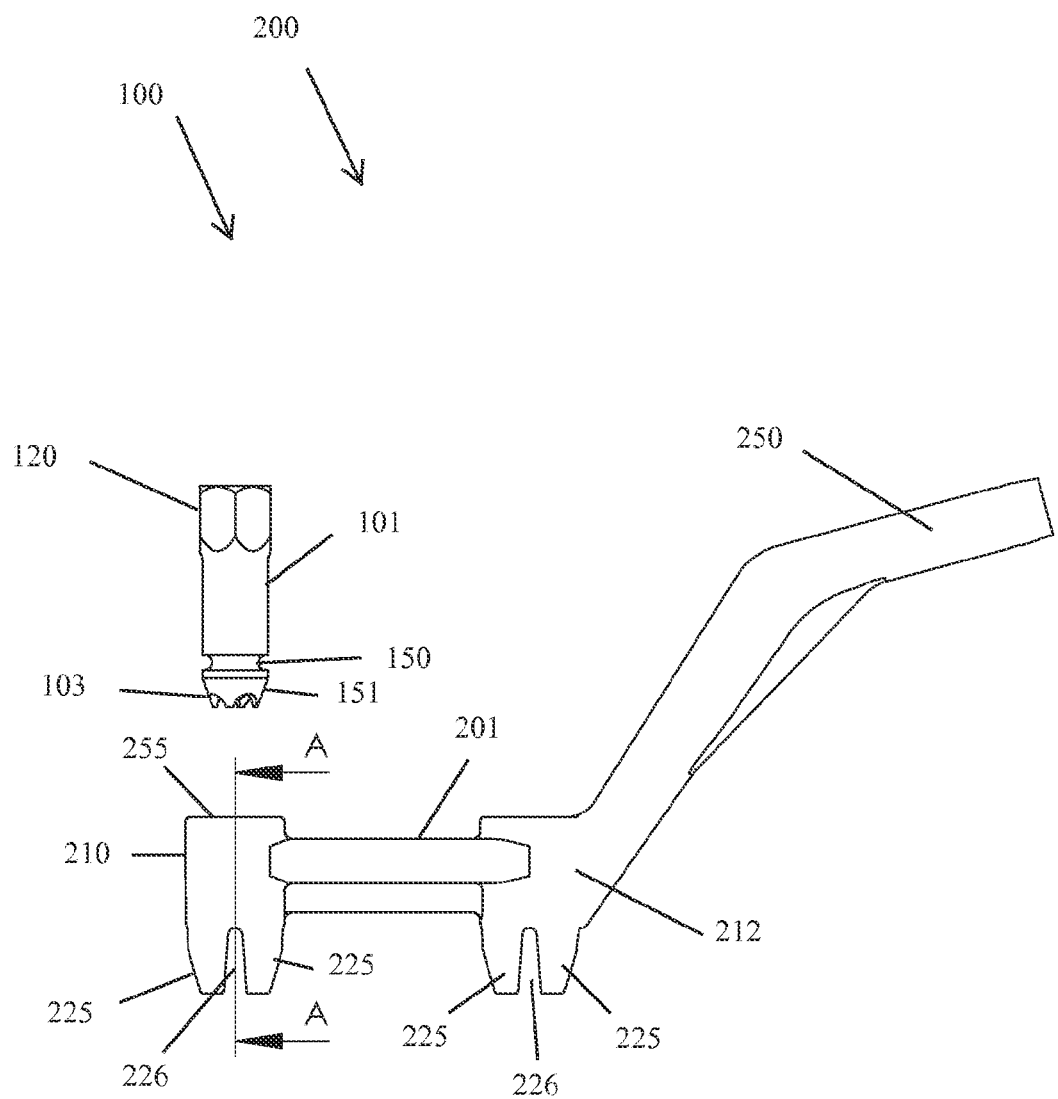
FIG. 3 is a side view illustrating the drill guide assembly with the drill guide insert suspended above the drill guide assembly.
Figure 4:
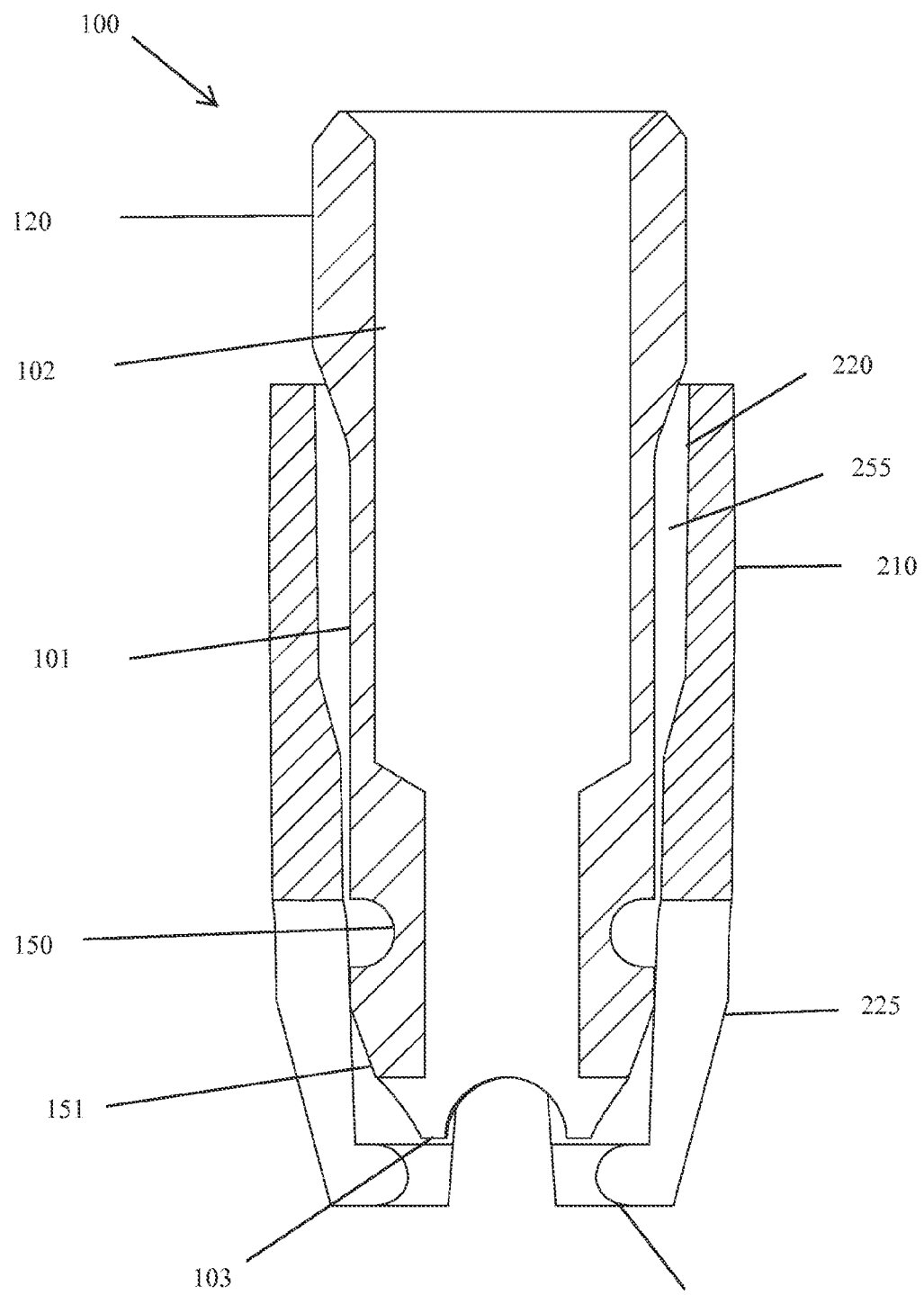
FIGS. 4-6 are cross-sectional views illustrating the installation of the drill guide insert into a drill guide body of the drill guide assembly.
Figure 5:
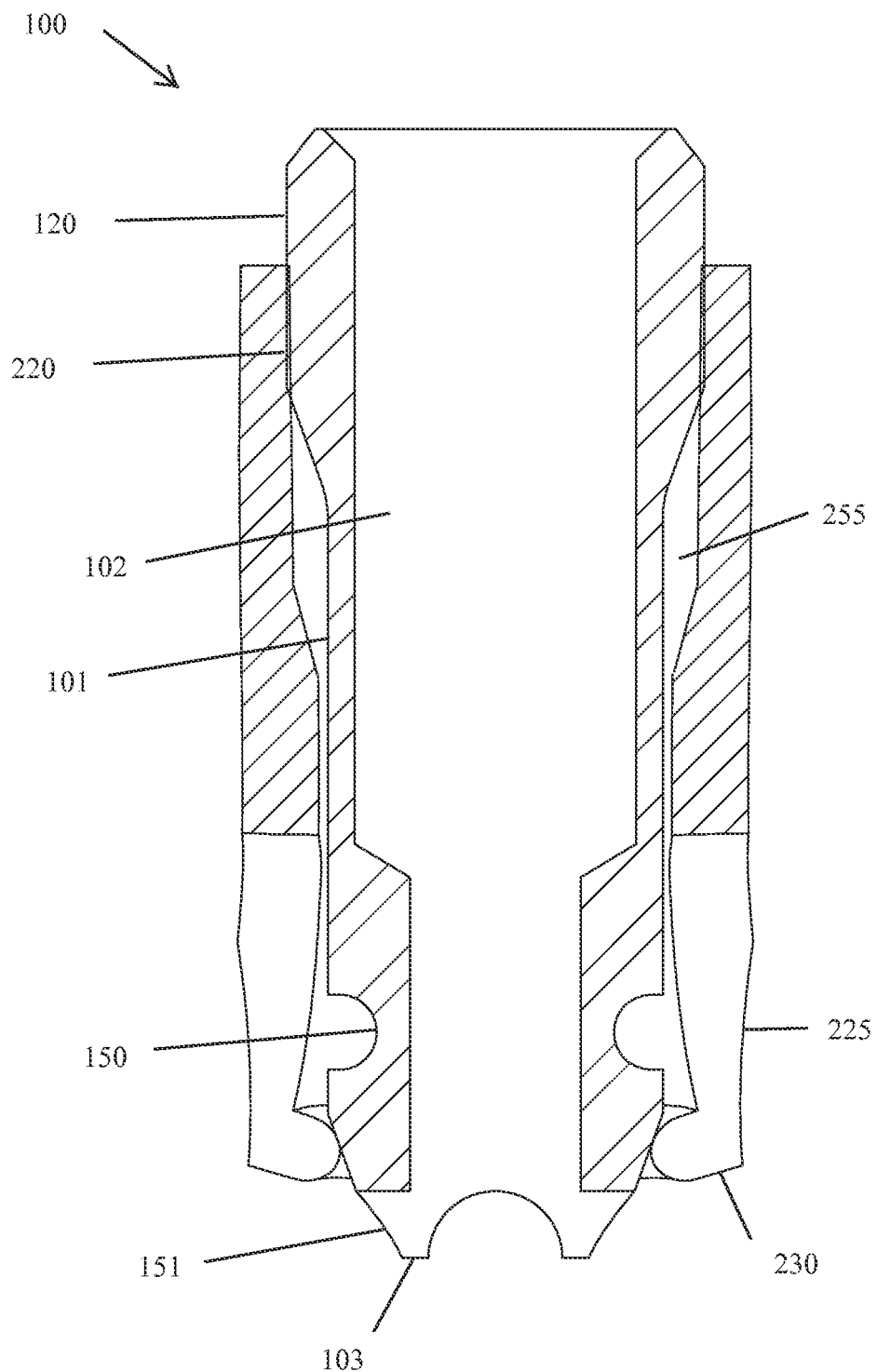

FIGS. 3-8 illustrate the installation of the drill guide insert 100 within the receiving passage 255 of the drill guide body 210. Only the installation of the drill guide insert 100 within the receiving passage 255 of the drill guide body 210 will be described herein on the basis the installation of a drill guide insert 100 into each of the receiving passages 255 of the drill guide bodies 211 and 212 is identical. In FIG. 3, the drill guide insert 100 is positioned above the drill guide body 210 such that the bone engagement surface 103 resides above the receiving passage 255. As illustrated in FIG. 4, the drill guide insert 100 enters the receiving passage 255 wherein the key member 120 engages the locking member 220. Furthermore, the grasping projection displacement surface 151 begins pushing against the engagement ridge 230 of the grasping projections 225 causing the grasping projections 225 to move from their closed to their open position as shown in FIG. 5.

Figure 6:
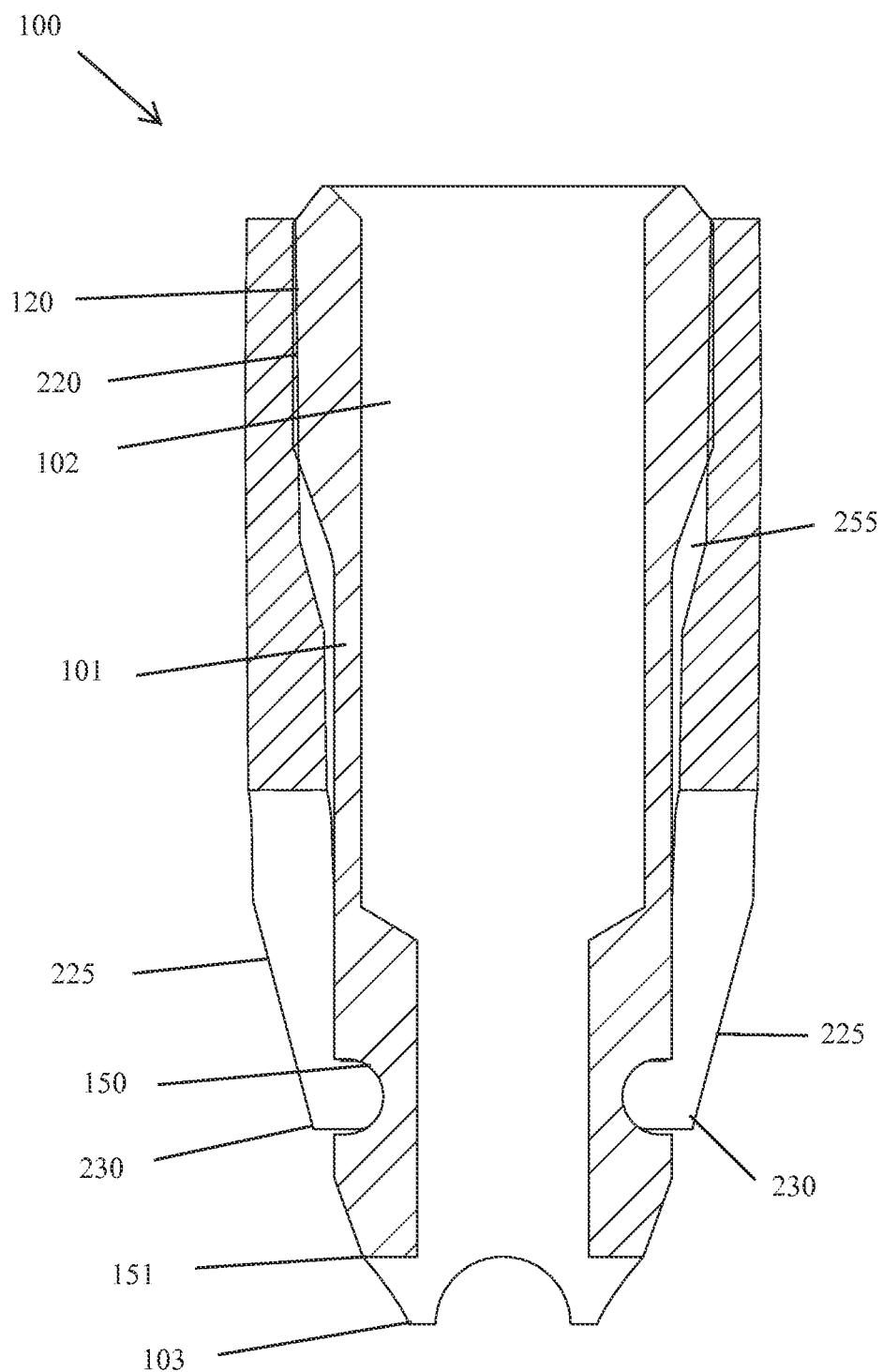

FIG. 6 illustrates the drill guide insert 100 fully installed within the drill guide body 210. As the drill guide insert 100 continues to install within the drill guide body 200, the engagement ridge 230 of the grasping projections 225 moves past the grasping projection displacement surface 151 and slips into the engagement groove 150 of the drill guide insert 100. Once the engagement ridge 230 slips into the engagement groove 150, the grasping projections 225 move from their open to their closed position thereby preventing the drill guide insert 100 from being pushed through or pulled out of the drill guide body 210. In addition, once the drill guide insert 100 fully installs within the drill guide body 210, the flat surfaces of the key member 120 fully engage the flat surfaces of the locking member 220 thereby preventing rotation of the drill guide insert 100 within the drill guide body 210.

Figure 7:
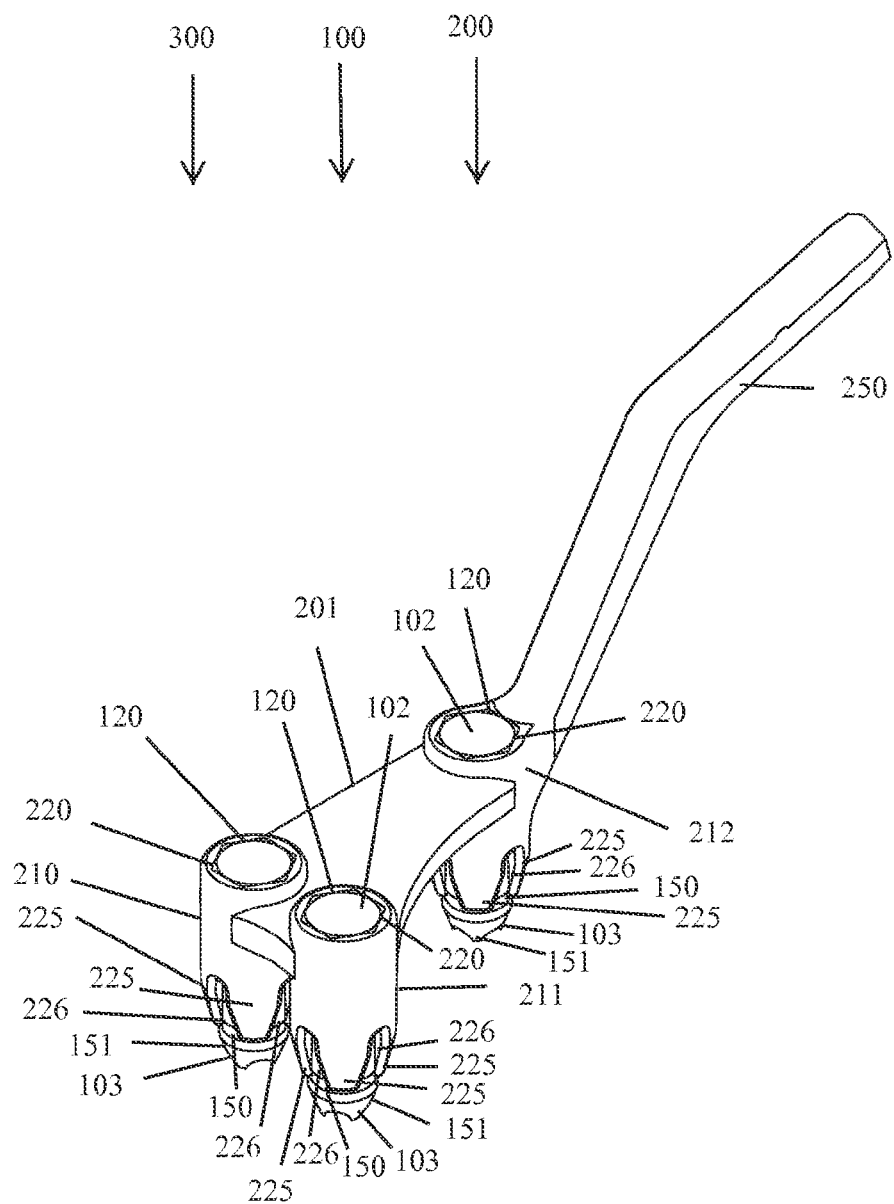
FIG. 7 is an isometric view illustrating a drill guide.
Figure 8:
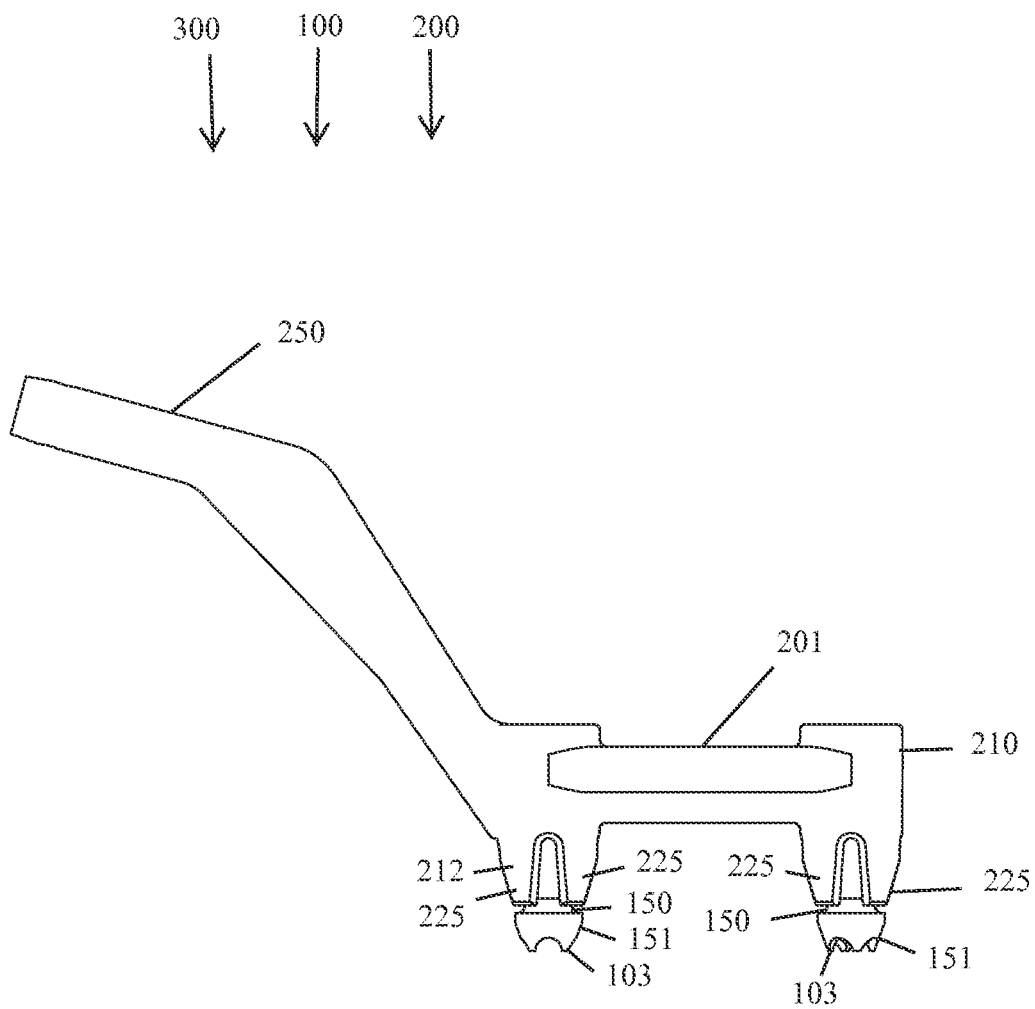
FIG. 8 is a side view illustrating the drill guide.

FIG. 7 illustrates the drill guide 300 fully assembled and ready for use. The operation of the drill guide 300 is as follows. The drill guide 300 is placed at an appropriate location on a bone such that the bone engagement surface 103 of the drill guide insert 100 engages the patient's bone. Pins are then placed within the receiving passages 255 of the drill guide bodies 210-212 to ensure that the drill guide 300 maintains its position on the bone. A surgeon then selects one of the drill guide bodies 210-212 to insert a drill bit. For illustrative purposes the surgeon selects drill guide body 210. The surgeon removes the pin, places a drill bit through the receiving passage 255 of the drill guide body 210, and begins drilling into the patient's bone. After drilling into the patient's bone, the surgeon selects the drill guide body 211 or 212 for drill bit insertion if more holes are required in the surgery. Once the surgeon has completed the drilling, the drill guide 300 is removed and the patient's bone is ready to receive the implant 50. The drilled holes are spaced apart the same as the distance among the legs 52-54 of the implant 50 such that the holes receive therein the legs 52-54 maintained in their open insertion position. The surgeon inserts the legs 52-54 and tamps down the implant 50 thereby securing the implant 50 to the patient's bone. Once secured to the patient's bone, the legs 52-54 of the implant 50 return to their closed implanted position thereby fusing the bone together and aiding the healing process.

A feature of the present invention is that the platform 201 of the drill guide body assembly 200 maintains the position of the drill guide bodies 210-212 such that the distances among the drill guide bodies 210-212 correspond to the distance among the legs 52-54 of the implant 50 in their open insertion position. Nevertheless, while the disclosed drill guide body assembly 200 includes the drill guide bodies 210-212, one of ordinary skill in the art will recognize that the number and spacing distance of drill guide bodies will correspond with the number of implant legs. Illustratively, a drill guide body assembly 200 for use with a two-legged implant will include two drill guide bodies spaced apart a distance equal to the distance between the two legs of the implant in their open insertion position. Likewise, a drill guide body assembly 200 for use with a four-legged implant will include four drill guide bodies spaced apart distances equal to the distances among the four legs of the implant in their open insertion position. Moreover, one of ordinary skill in the art will recognize that an implant with a single insertion point would require a drill guide body assembly 200 having only a single drill guide body.

Although the present invention has been described in terms of the foregoing preferred embodiments, such description has been for exemplary purposes only and, as will be apparent to those of ordinary skill in the art, many alternatives, equivalents, and variations of varying degrees will fall within the scope of the present invention. That scope, accordingly, is not to be limited in any respect by the foregoing detailed description; rather, it is defined only by the claims that follow.

The invention claimed is:

1. A drill guide, comprising:
   a drill guide assembly, comprising a first drill guide body defining a receiving passage, wherein the first drill guide body includes a locking member comprised of individual surfaces in the receiving passage, further wherein the first drill guide body terminates in a first grasping projection adapted for flexing between an open position and a closed position;
   a shaft securable to the drill guide assembly;
   a first drill guide insert defining a bore and adapted for insertion into the receiving passage of the first drill guide body, the first drill guide insert including:
      a grasping projection displacement surface adapted to engage and move the first grasping projection from its closed position to its open position during initial insertion of the first drill guide insert into the receiving passage of the first drill guide body,
      a locking groove disposed at a distal end of the first drill guide insert, the locking groove being adapted to receive therein the first grasping projection of the first drill guide body, wherein, upon continued insertion of the first drill guide insert into the receiving passage of the first drill guide body, the grasping projection displacement surface disengages from the first grasping projection such that the first grasping projection moves from its open position to its closed position, further wherein the first grasping projection engages the locking groove thereby preventing the first drill guide insert from being pushed through or pulled out of the receiving passage of the first drill guide body, and
      a key member disposed at a proximal end of the first drill guide insert, the key member comprising individual surfaces adapted to engage the individual surfaces of the locking member of the first drill guide body upon insertion of the first drill guide insert into the receiving passage of the first drill guide body, wherein engagement of the individual surfaces of the key member and the locking member prevents rotation of the first drill guide insert within the receiving passage of the first drill guide body.

2. The drill guide according to claim 1, wherein the drill guide assembly further comprises:
   a second drill guide body defining a receiving passage, wherein the second drill guide body includes a locking member and terminates in a first grasping projection adapted for flexing between an open position and a closed position; and
   a platform connecting the first drill guide body with the second drill guide body, wherein the platform spaces the first drill guide body apart from the second drill guide body a distance substantially equal to a distance between first and second legs of an implant residing in an open insertion position.

3. The drill guide according to claim 2, wherein the drill guide further comprises:
   a second drill guide insert defining a bore and adapted for insertion into the receiving passage of the second drill guide body, the second drill guide insert including:
      a grasping projection displacement surface adapted to engage and move the first grasping projection from its closed position to its open position during initial insertion of the second drill guide insert into the receiving passage of the second drill guide body,
      a locking groove adapted to receive therein the first grasping projection of the second drill guide body, wherein, upon continued insertion of the second drill guide insert into the receiving passage of the second drill guide body, the grasping projection displacement surface disengages from the first grasping projection such that the second grasping projection moves from its open position to its closed position, further wherein the first grasping projection engages the locking groove thereby preventing the second drill guide insert from being pushed through or pulled out of the receiving passage of the second drill guide body, and
      a key member adapted to engage the locking member of the second drill guide body upon insertion of the second drill guide insert into the receiving passage of the second drill guide body, wherein the key member and the locking member engage to prevent rotation of the second drill guide insert within the receiving passage of the second drill guide body.

4. The drill guide according to claim 3, wherein the drill guide assembly further comprises:
   a third drill guide body defining a receiving passage, wherein the third drill guide body includes a locking member and terminates in a first grasping projection adapted for flexing between an open position and a closed position; and
   the platform connecting the first, second and third drill guide bodies, wherein the platform spaces the first, second, and third drill guide bodies apart from each other distances substantially equal to distances among first, second, and third legs of an implant residing in an open insertion position.

5. The drill guide according to claim 4, wherein the drill guide further comprises:
   a third drill guide insert defining a bore and adapted for insertion into the receiving passage of the third drill guide body, the third drill guide insert including:
      a grasping projection displacement surface adapted to engage and move the first grasping projection from its closed position to its open position during initial insertion of the third drill guide insert into the receiving passage of the third drill guide body,
      a locking groove adapted to receive therein the first grasping projection of the third drill guide body, wherein, upon continued insertion of the third drill guide insert into the receiving passage of the third drill guide body, the grasping projection displacement surface disengages from the first grasping projection such that the second grasping projection moves from its open position to its closed position, further wherein the first grasping projection engages the locking groove thereby preventing the third drill guide insert from being pushed through or pulled out of the receiving passage of the third drill guide body, and
      a key member adapted to engage the locking member of the third drill guide body upon insertion of the third drill guide insert into the receiving passage of the third drill guide body, wherein the key member and the locking member engage to prevent rotation of the third drill guide insert within the receiving passage of the third drill guide body.

6. The drill guide according to claim 4, wherein the third drill guide body includes a first slot and second slot with the first grasping projection therebetween, further wherein the first and second slots allow the first grasping projection to flex between the open position and the closed position.

7. The drill guide according to claim 2, wherein the second drill guide body includes a first slot and second slot with the first grasping projection therebetween, further wherein the first and second slots allow the first grasping projection to flex between the open position and the closed position.

8. The drill guide according to claim 1, wherein the first drill guide body includes a first slot and second slot with the first grasping projection therebetween, further wherein the first and second slots allow the first grasping projection to flex between the open position and the closed position.

9. The drill guide according to claim 1, wherein the drill guide is used in combination with an implant, comprising a first leg and a second leg having a body therebetween, wherein the first leg and the second leg are movable between an closed implanted position and an open insertion position.

10. The drill guide according to claim 9, wherein the drill guide assembly further comprises:
a second drill guide body defining a receiving passage, wherein the second drill guide body includes a locking member and terminates in a first grasping projection adapted for flexing between an open position and a closed position; and
a platform connecting the first drill guide body with the second drill guide body, wherein the platform spaces the first drill guide body apart from the second drill guide body a distance substantially equal to a distance between the first and second legs of the implant residing in their open insertion position.

11. The drill guide according to claim 10, wherein the drill guide further comprises:
a second drill guide insert defining a bore and adapted for insertion into the receiving passage of the second drill guide body, the second drill guide insert including:
a grasping projection displacement surface adapted to engage and move the first grasping projection from its closed position to its open position during initial insertion of the second drill guide insert into the receiving passage of the second drill guide body,
a locking groove adapted to receive therein the first grasping projection of the second drill guide body, wherein, upon continued insertion of the second drill guide insert into the receiving passage of the second drill guide body, the grasping projection displacement surface disengages from the first grasping projection such that the second grasping projection moves from its open position to its closed position, further wherein the first grasping projection engages the locking groove thereby preventing the second drill guide insert from being pushed through or pulled out of the receiving passage of the second drill guide body, and
a key member adapted to engage the locking member of the second drill guide body upon insertion of the second drill guide insert into the receiving passage of the second drill guide body, wherein the key member and the locking member engage to prevent rotation of the second drill guide insert within the receiving passage of the second drill guide body.

12. The drill guide according to claim 1, wherein the drill guide is used in combination with an implant, comprising a first leg, a second leg, and a third leg having a body therebetween, wherein the first leg, the second leg, and the third leg are movable between an closed implanted position and an open insertion position.

13. The drill guide according to claim 12, wherein the drill guide assembly further comprises:
a second drill guide body defining a receiving passage, wherein the second drill guide body includes a locking member and terminates in a first grasping projection adapted for flexing between an open position and a closed position;
a third drill guide body defining a receiving passage, wherein the third drill guide body includes a locking member and terminates in a first grasping projection adapted for flexing between an open position and a closed position; and
platform connecting the first, second and third drill guide bodies, wherein the platform spaces the first, second, and third drill guide bodies apart from each other distances substantially equal to distances among the first, second, and third legs of the implant residing in their open insertion position.

14. The drill guide according to claim 13, wherein the drill guide further comprises:
a second drill guide insert defining a bore and adapted for insertion into the receiving passage of the second drill guide body, the second drill guide insert including:
a grasping projection displacement surface adapted to engage and move the first grasping projection from its closed position to its open position during initial insertion of the second drill guide insert into the receiving passage of the second drill guide body,
a locking groove adapted to receive therein the first grasping projection of the second drill guide body, wherein, upon continued insertion of the second drill guide insert into the receiving passage of the second drill guide body, the grasping projection displacement surface disengages from the first grasping projection such that the second grasping projection moves from its open position to its closed position, further wherein the first grasping projection engages the locking groove thereby preventing the second drill guide insert from being pushed through or pulled out of the receiving passage of the second drill guide body, and
a key member adapted to engage the locking member of the second drill guide body upon insertion of the second drill guide insert into the receiving passage of the second drill guide body, wherein the key member and the locking member engage to prevent rotation of the second drill guide insert within the receiving passage of the second drill guide body; and
a third drill guide insert defining a bore and adapted for insertion into the receiving passage of the third drill guide body, the third drill guide insert including:
a grasping projection displacement surface adapted to engage and move the first grasping projection from its closed position to its open position during initial insertion of the third drill guide insert into the receiving passage of the third drill guide body,
a locking groove adapted to receive therein the first grasping projection of the third drill guide body, wherein, upon continued insertion of the third drill guide insert into the receiving passage of the third drill guide body, the grasping projection displacement surface disengages from the first grasping projection such that the second grasping projection moves from its open position to its closed position, further wherein the first grasping projection engages the locking groove thereby preventing the third drill guide insert from being pushed through or pulled out of the receiving passage of the third drill guide body, and a key member adapted to engage the locking member of the third drill guide body upon insertion of the third drill guide insert into the receiving passage of the third drill guide body, wherein the key member and the locking member engage to prevent rotation of the third drill guide insert within the receiving passage of the third drill guide body.

\* \* \* \* \*